United States Patent
Schotland et al.

(10) Patent No.: US 6,775,349 B2
(45) Date of Patent: Aug. 10, 2004

(54) SYSTEM AND METHOD FOR SCANNING NEAR-FIELD OPTICAL TOMOGRAPHY

(75) Inventors: John Carl Schotland, Ladue, MO (US); Paul Scott Carney, Champaign, IL (US)

(73) Assignee: Washington Univ. in St. Louis, St. Louis, MO (US)

( * ) Notice: Subject to any disclaimer, the term of this patent is extended or adjusted under 35 U.S.C. 154(b) by 448 days.

(21) Appl. No.: 10/045,274

(22) Filed: Oct. 23, 2001

(65) Prior Publication Data

US 2003/0099329 A1 May 29, 2003

(51) Int. Cl.[7] .............................................. H05G 1/00
(52) U.S. Cl. ...................... 378/21; 378/4; 250/370.08
(58) Field of Search ............................ 378/4, 15, 21, 378/22, 901; 250/370.08

(56) References Cited

U.S. PATENT DOCUMENTS

| | | |
|---|---|---|
| 5,286,970 A | 2/1994 | Betzig et al. |
| 5,382,789 A | 1/1995 | Aoshima |
| 5,479,024 A | 12/1995 | Hillner et al. |
| 5,485,536 A | 1/1996 | Islam |
| 6,618,463 B1 * | 9/2003 | Schotland et al. ............ 378/21 |
| 2002/0021451 A1 * | 2/2002 | Hill ............................ 356/511 |

OTHER PUBLICATIONS

Influence of dielectric contrast and topography on the near field scattered by an inhomogeneous surface, by Carminati et al. J. Opt. Sco. Am. A/vol. 12, Dec. 1995 pp. 2716–2725.

U.S. patent application, Ser. No. 09/490,615; filed Jan. 25, 2000 Applicant: Schotland Case 6.

* cited by examiner

Primary Examiner—David V Bruce

(57) ABSTRACT

A method for the reconstruction of a tomographic image of an object from measurements of scattering data resulting from probing waves. The scattering data is related to a forward scattering operator by an integral operator. The tomographic image is reconstructed by executing a prescribed mathematical algorithm, as determined with reference to the integral operator, on the scattering data.

30 Claims, 5 Drawing Sheets

SYSTEM AND METHOD FOR SCANNING NEAR-FIELD OPTICAL TOMOGRAPHY

BACKGROUND OF THE INVENTION

1. Field of the Invention

This invention relates to tomography and, more particularly, to near-field microscopy wherein an image of an object is directly reconstructed with sub-wavelength resolution.

2. Description of the Background Art

Near-field scanning optical microscopy (NSOM) is a technique to obtain images of surfaces with sub-wavelength resolution. The technique is particularly important for imaging structures where spectroscopic concerns or sample handling requirements dictate the use of lower frequency fields and yet high spatial resolution is still required. Applications range from the inspection of organic and biological samples to semiconductors. Various modalities are in practical use. Two prominent examples of such modalities are "illumination mode NSOM" and "collection mode NSOM". In illumination mode NSOM, a tapered fiber probe with a sub-wavelength size aperture serves as a source of illumination in the near-zone of the sample. The scattered field intensity is then measured and recorded as a function of the probe position while the probe is scanned over the sample. In collection mode NSOM, the fiber probe serves to detect the scattered field in the near-zone as the sample is illuminated by a source in the far zone.

There are certain limitations of current NSOM techniques. Despite the fact that the sample may present a complicated three-dimensional structure, NSOM produces only a two-dimensional image of the sample. Indeed, rather than being an imaging method, it is more accurate to say that NSOM maps the sub-wavelength structure of the optical near-field intensity. Under certain simplifying assumptions, such as homogeneity of the bulk optical properties of the sample, the maps produced in these experiments may be related to the sample structure. However, for the more general case in which the topography of the sample and the bulk optical properties both vary, the connection between the near-field intensity and the sample structure can be ambiguous.

To resolve this ambiguity it is desirable to solve the inverse scattering problem (ISP). The ISP may be characterized as reconstructing the three-dimensional object structure, in this case the dielectric susceptibility of the sample, from measurements of the scattered field. By solving the ISP, two main issues of the prior art are resolved, namely, the ambiguity in connecting the sample properties and the measured data is resolved, and simultaneously three-dimensional, tomographic images of the sample are obtained.

Historically, solving the ISP for other scattering modalities has greatly expanded the functionality of existing methods. For instance, pioneering analysis of X-ray diffraction made modem crystallography a reality. Another pioneering work brought medical imaging out of the era of projection radiography and into the era of computed tomography (CT). In any ISP the first step is to obtain a physically reasonable forward model for the scattering process. For instance, in CT, a geometric model of propagation, neglecting any scattering, sufficiently describes the experiment. Likewise, as scattering becomes important, the first Born approximation is a reasonable model. By considering the far-zone scattered field, one may obtain a readily soluble ISP, now generally known as diffraction tomography (DT). The crucial step in the DT solution is to obtain a linearized relationship between the sample properties and the scattered field or some simple function of the scattered field. This may be accomplished by making use of models such as the first Born or first Rytov approximations. Solutions for the nonlinear ISP may be obtained as well, but in general they suffer from mathematical pathologies involving convergence.

The far-zone ISP has an inherent resolution limit imposed by the wavelength of the probe field. This limit may be traced to the fact that only the homogeneous part of the scattered field contributes to the far-zone. While in principle a higher resolution image may be obtained by mathematical extrapolation, this approach is exponentially sensitive to errors in the scattering data. However, the evanescent waves which contribute to the near-field carry the higher spatial frequency information about the scatterer. It is known that inclusion of the evanescent waves in the standard back propagation algorithm of two-dimensional DT enhances the resolving power of that method.

The sub-wavelength resolution obtained in NSOM arises because direct access to the evanescent scattered waves by probing the near-field is effected. It is this part of the scattered field on which the sub-wavelength structure of the scattering object is encoded. The NSOM ISP is thus of great interest because it obtains sub-wavelength resolved three-dimensional reconstructions. This technique, in accordance with the present invention, is referred to this as "scanning near-field optical tomography".

Representative of the art in this technological area are the following U.S. patents: (a) Fiber Optic Probe for Near Field Optical Microscopy (U.S. Pat. No. 5,485,536); (b) Method and Apparatus for Performing Near-Field Optical Microscopy (U.S. Pat. No. 5,479,024); (c) Near Field Scanning Tunneling Optical Microscope (U.S. Pat. No. 5,382,789; and (d) Near Field Optical Microscopic Examination of a Biological Specimen (U.S. Pat. No. 5,286,970).

The art is devoid of any teachings or suggestions for treating the inverse scattering problem which is applicable to the near-field case.

SUMMARY OF THE INVENTION

These shortcomings, as well as other limitations and deficiencies are obviated, in accordance with the present invention, by devising explicit inversion formulas that are applicable to near-field scanning optical tomography and which provide a direct reconstruction of a scattering potential associated with a sample being scanned.

In accordance with a broad method aspect of the present invention related to scalar waves, an image of an object is generated by: (a) probing the object with incident scalar waves; (b) detecting scattered waves from the object, wherein the scattered waves are detected in a near-field collection mode; and (c) reconstructing the tomographic image by executing a prescribed mathematical algorithm with reference to the incident scalar waves and the scattered waves to generate the tomographic image with sub-wavelength spatial resolution.

In accordance with another broad method aspect of the present invention related to scalar waves, an image of an object is generated by: (a) probing the object with incident scalar waves, wherein the incident scalar waves are generated in a near-field illumination mode; (b) detecting scattered waves from the object, wherein the scattered waves are detected in the far-field of the object; and (c) reconstructing the tomographic image by executing a prescribed mathematical algorithm with reference to the incident scalar waves and the scattered waves to generate the tomographic image with sub-wavelength spatial resolution.

In accordance with yet another broad method aspect of the present invention related to scalar waves, an image of an object is generated by: (a) probing the object with incident scalar waves, wherein the incident scalar waves are generated in a near-field illumination mode; (b) detecting scattered waves from the object, wherein the scattered waves are detected in a near-field collection mode; and (c) reconstructing the tomographic image by executing a prescribed mathematical algorithm with reference to the incident scalar waves and the scattered waves to generate the image with sub-wavelength spatial resolution.

In accordance with a broad method aspect of the present invention related to electromagnetic waves, an image of an object is generated by: (a) probing the object with incident electromagnetic waves; (b) detecting scattered waves from the object, wherein the scattered waves are detected in a near-field collection mode; and (c) reconstructing the tomographic image by executing a prescribed mathematical algorithm with reference to the incident electromagnetic waves and the scattered waves to generate the tomographic image with sub-wavelength spatial resolution.

In accordance with another broad method aspect of the present invention related to electromagnetic waves, an image of an object is generated by: (a) probing the object with incident electromagnetic waves, wherein the incident electromagnetic waves are generated in a near-field illumination mode; (b) detecting scattered waves from the object, wherein the scattered waves are detected in the far-field of the object; and (c) reconstructing the tomographic image by executing a prescribed mathematical algorithm with reference to the incident electromagnetic waves and the scattered waves to generate the tomographic image with sub-wavelength spatial resolution.

In accordance with yet another broad method aspect of the present invention related to electromagnetic waves, an image of an object is generated by: (a) probing the object with incident electromagnetic waves, wherein the incident electromagnetic waves are generated in a near-field illumination mode; (b) detecting scattered waves from the object, wherein the scattered waves are detected in a near-field collection mode; and (c) reconstructing the tomographic image by executing a prescribed mathematical algorithm with reference to the incident electromagnetic waves and the scattered waves to generate the image with sub-wavelength spatial resolution.

Broad system aspects of the present invention are commensurate with these method aspects.

DETAILED DESCRIPTION

1. Overview

Figure 1:
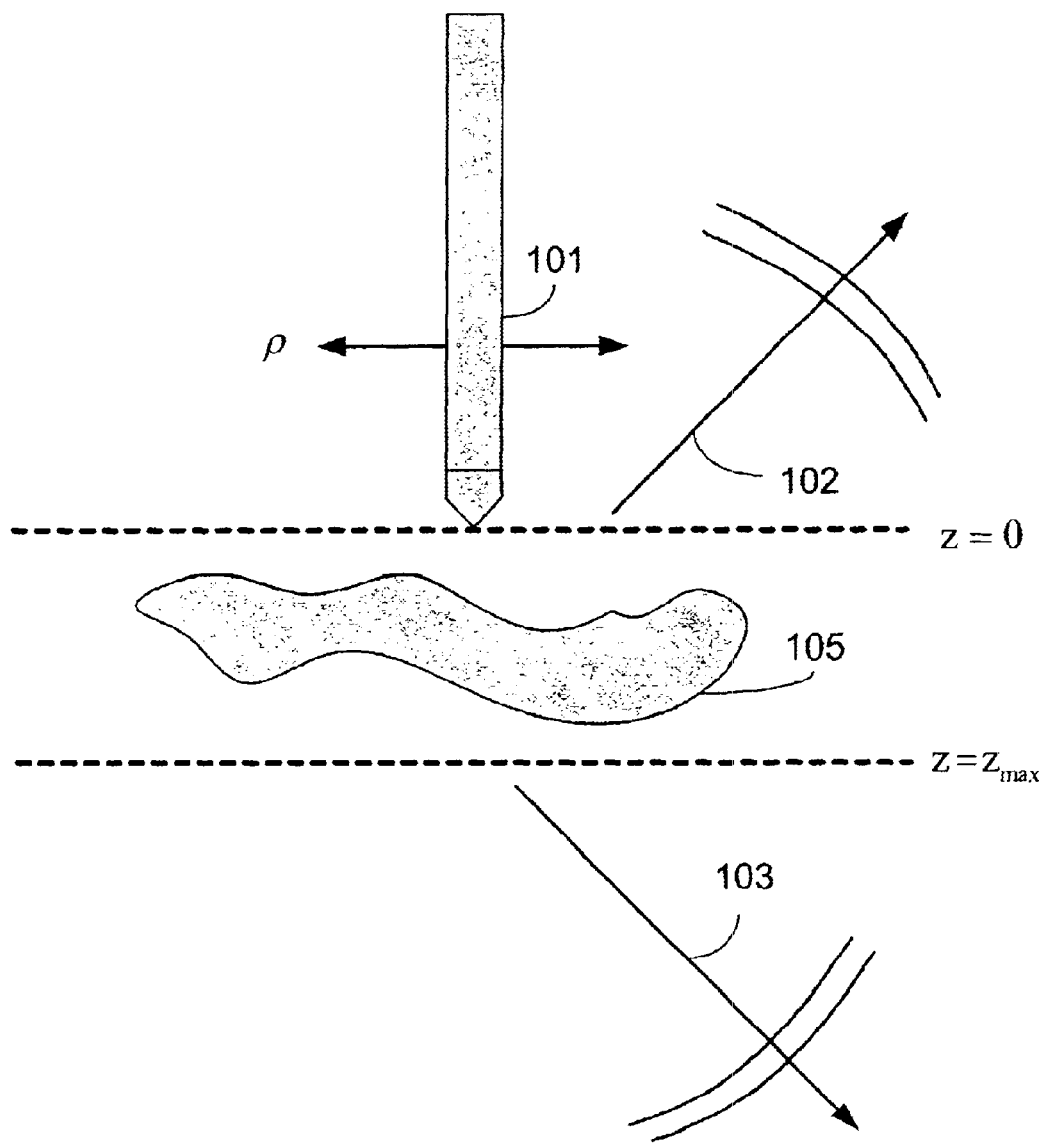
FIG. 1 is a pictorial representation for the single probe illumination mode showing an object under test.

When both the phase and amplitude of the optical near-field are measurable, the near-field ISP may be solved, and robust inversion algorithms for both the scalar and vector near-field scattered waves may be obtained. In this detailed description, three example modalities are treated. The treatment of the vector case is particularly important in the near-field ISP because polarization effects are somewhat more complicated than for the far-field problem. The solution in all cases is derived by a singular value decomposition (SVD) analysis of the linearized scattering problem. The SVD is a generalized mode decomposition that offers considerable insight into the scattering problem.

In Section 2, a discussion of near-field scattering for scalar wave-fields obeying the scalar reduced wave equation is presented. Specifically, expressions for the scattered field as measured in three distinct modalities are obtained. The first two modalities are variations on the illumination mode and collection mode techniques. It is presumed that the field may be measured, that is, the measurements are phase sensitive. Moreover, the third modality requires the use of two near-field probes. The three expressions derived for the scattered fields are shown to be special cases of a single expression relating the measured data to the structure of the scattering object to be imaged.

In Section 3, a unified form for all three modalities is treated and it is shown that, in all cases, a unique solution of the inverse scattering problem exists. Furthermore, the SVD for the scattering kernel is then developed and the inversion formula for the ISP is obtained.

In Section 4 the vector theory of near-field scattering is presented. The three modalities are again discussed, as well as the unified form of the modalities.

In Section 5, the existence and uniqueness of the solution to the inverse scattering problem is demonstrated and the SVD is developed. It will be seen that though the vector nature of light makes a significant difference in the physics of the problem, the underlying mathematical form is much like the scalar case and the results follow from the scalar case in a straight-forward manner.

2. Function Theoretic Basis for Scalar Scattering

To understand the principles in accordance with the present invention, the case wherein a monochromatic scalar plane wave of frequency $\omega$ incident on a medium characterized by a scattering potential $\eta(r)$ is first considered. The field U(r) of the wave satisfies the reduced wave equation $$\nabla^2 U(r)+k_0^2 U(r)=-4\pi k_0^2 \eta(r) U(r) \qquad (1)$$

where $k_0^2=2\pi/\lambda=\omega/c$ is the free-space wavenumber of the incident wave. The field is then composed of two parts, namely, $$U(r)=U_i(r)+U_s(r), \qquad (2)$$

with the incident field $U_i(r)$ satisfying the free-space reduced wave equation, $$\nabla^2 U_i(r)+k_0^2 U_i(r)=0, \qquad (3)$$

and the scattered field $U_s(r)$ satisfying the equation $$\nabla^2 U_s(r)+k_0^2 U_s(r)=-4\pi k_0^2 \eta(r) U(r). \qquad (4)$$

Following standard procedures, equation (4) may be recast as the integral equation $$U_s(r)=k_0^2 \int d^3 r' G(r-r')\eta(r')U(r'), \qquad (5)$$

where $$G(r-r') = \frac{1}{4\pi} \frac{e^{ik_0|r-r'|}}{|r-r'|} \quad (6)$$

is the outgoing-wave Green's function for equation (4) which obeys $$\nabla^2 G(r) + k_0^2 G(r) = -4\pi\delta(r). \quad (7)$$

If the scattered field is much weaker than the incident wave, the first Born approximation applies and the following is obtained from equation (5):

$$U_s(r) = k_0^2 \int d^3r' G(r-r') \eta(r') U_i(r'). \quad (8)$$

In the discussion that follows, it will prove useful to express the Green's function G in the plane wave decomposition $$G(r) = \frac{i}{2\pi} \int d^2Q k_z(Q)^{-1} \exp[iQ \cdot \rho + ik_z(Q)|z|], \quad (9)$$

where $k_z(Q) = (k_0^2 - Q^2)^{1/2}$. The modes appearing in equation (9) labeled by Q for which $|Q| \leq k_0$ are the homogeneous wave modes. The modes labeled by Q for which $|Q| > k_0$ are evanescent. For these modes, $k_z(Q) = i|k_z(Q)|$ so that the evanescent waves decay exponentially on propagation, with a concomitant loss of high-spatial frequency components in the scattered field.

2A. Illumination Mode

Next consider the case in which the sample is illuminated by a point source with unit amplitude at the position $r_1$ with $$U_i(r) = \frac{e^{ik_0|r-r_1|}}{|r-r_1|}. \quad (10)$$

This arrangement is shown pictorially in FIG. 1 wherein probe 101 is representative of a source which illuminates sample 105. The illumination as reflected from sample 105 is depicted by reflected wave 102, and the illumination as transmitted by sample 105 is depicted by transmitted wave 103.

The scattered field at a point r is then given by the expression $$U_s(r) = k_0^2 \int d^3r' G(r-r') \eta(r') G(r'-r_1). \quad (11)$$

It is assumed that the source lies in the plane z=0 so that the position of the source is $r_1 = (\rho_1, 0)$ with $\rho_1$ being the transverse coordinate of the source. The scatterer is assumed to lie only in the half-space $z \geq 0$ and to be of finite range. If the scattered field is measured in the z>0 half-space, this scattered field is referred to as the "transmission mode". If the scattered field is measured in the $z \leq 0$ half-space, this scattered field is referred to as the "reflection mode". It is now supposed that the observation point r is very far from the domain of the scatterer. Then observe that for $|r| \gg |r'|$ $$G(r-r') \sim \frac{e^{ik_0 r}}{r} e^{-ik(q)r'} \quad (12)$$

where $k(q) = (q, \epsilon k_z(q))$ is parallel to r. Here $\epsilon = 1$ for the transmission mode, and $\epsilon = -1$ for the reflection mode. It is then seen that the scattered field may be expressed in terms of the scattering amplitude $A(\rho_1, q)$ as $$U_s(r) \sim \frac{e^{ik_0 r}}{r} A(\rho_1, q), \quad (13)$$

where with the use of equations (9), (11), and (12) it is found that $$A(\rho_1, q) = k_0^2 \int d^3r' G(r'-r_1) \exp[-iq \cdot \rho' - i\epsilon k_z(q)z'] \eta(r'). \quad (14)$$

Now define a data function $\Phi_1(q_1, q_2)$ by a two-dimensional Fourier transform of $A(\rho_1, q)$, $$\Phi_1(q_1, q_2) = \frac{1}{2\pi} \int d^2\rho_1 e^{iq_1 \rho_1} A(\rho_1, q_2). \quad (15)$$

Making use of equations (9) and (14), it is readily shown that $$\Phi_1(q_1, q_2) = \frac{ik_0^2}{k_z(q_1)} \int d^3r \exp\{i(q_1 - q_2) \cdot \rho + i[k_z(q_1) - \epsilon k_z(q_2)]z\} \eta(r). \quad (16)$$

2B. Collection Mode

Figure 2:
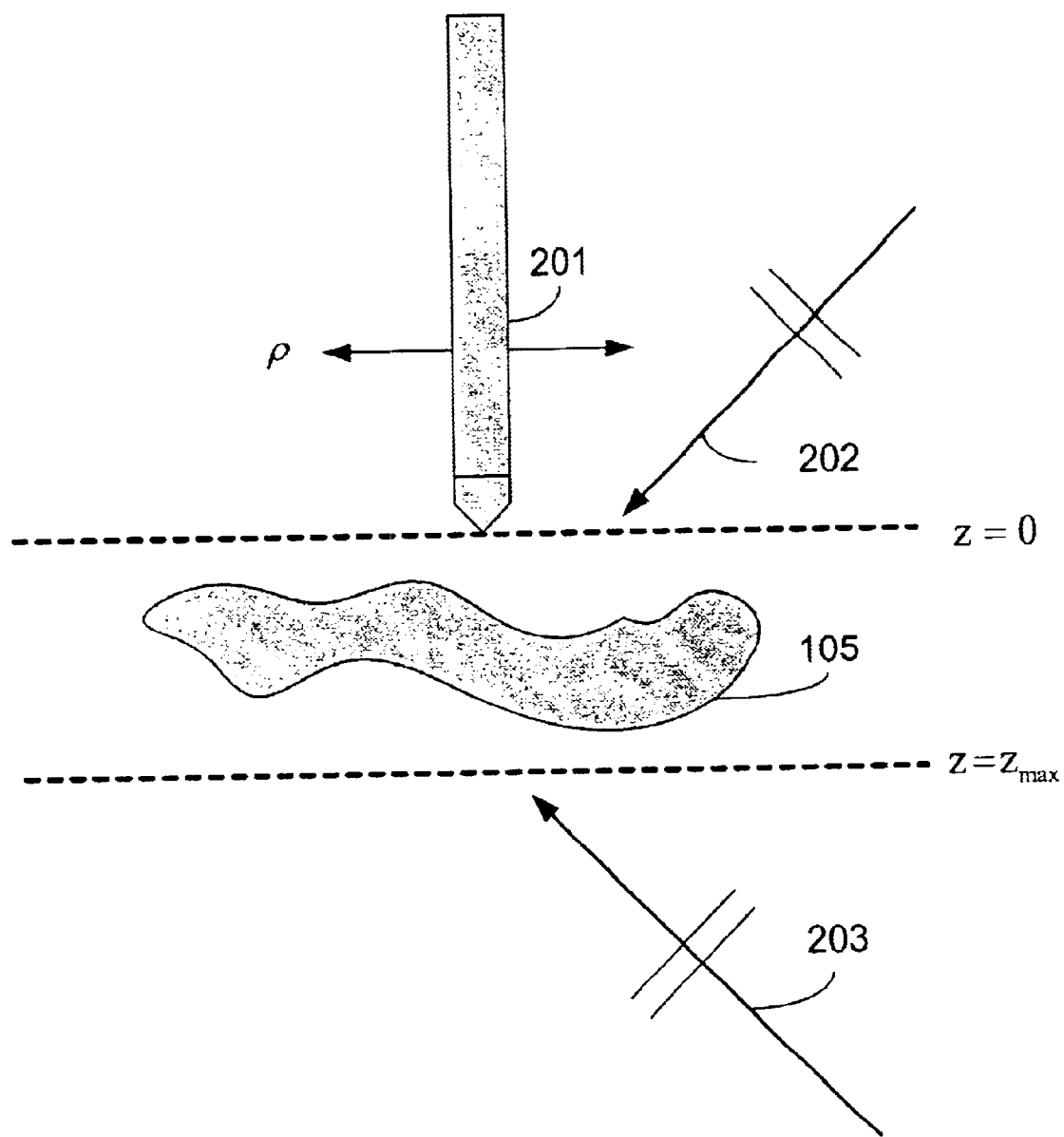
FIG. 2 is a pictorial representation for the single probe collection mode showing an object under test.

In this modality, the sample 105 is illuminated from the far zone by an incident plane wave and the scattered field is detected in the near-zone by means of an idealized point detector. This arrangement is shown pictorially in FIG. 2 wherein probe 201 is representative of a detector which collects scattered waves from sample 105. Sample 105 is illuminated by incident wave 202 in the reflection mode, whereas sample 105 is illuminated by incident wave 203 in the transmission mode.

The incident wave is taken to have unit amplitude and is of the form $$U_i(r) = \exp[iq \cdot \rho - i\epsilon k_z(q)z], \quad (17)$$

where, once again, $\epsilon = 1$ for the transmission mode and $\epsilon = -1$ for the reflection mode. The scattered field, measured in the z=0 plane at a point with transverse coordinate $\rho$, is given by the expression $$U_s(\rho, 0; q) = k_0^2 \int d^3r' \exp[iq \cdot \rho' - i\epsilon k_z(q)z] G(r'-r) \eta(r'), \quad (18)$$

which follows from equation (8). As in the illumination mode case, a data function $\Phi_2(q_1, q_2)$ is defined by a Fourier transform of the scattered field $$\Phi_2(q_1, q_2) = \frac{1}{2\pi} \int d^2\rho e^{-iq_2 \cdot \rho} U_s(\rho, 0; q_1). \quad (19)$$

Making use of the plane wave mode representation of the Green's function of equation (9), it is found that $$\Phi_2(q_1, q_2) = \frac{ik_0^2}{k_z(q_2)} \int d^3r \exp\{i(q_1 - q_2) \cdot \rho + i[k_z(q_2) - \epsilon k_z(q_1)]z\} \eta(r). \quad (20)$$

It is seen that $\Phi_2(q_1, q_2) = \Phi_1(-q_2, -q_1)$, as expected from reciprocity.

2C. Two Probe Mode

Figure 3:
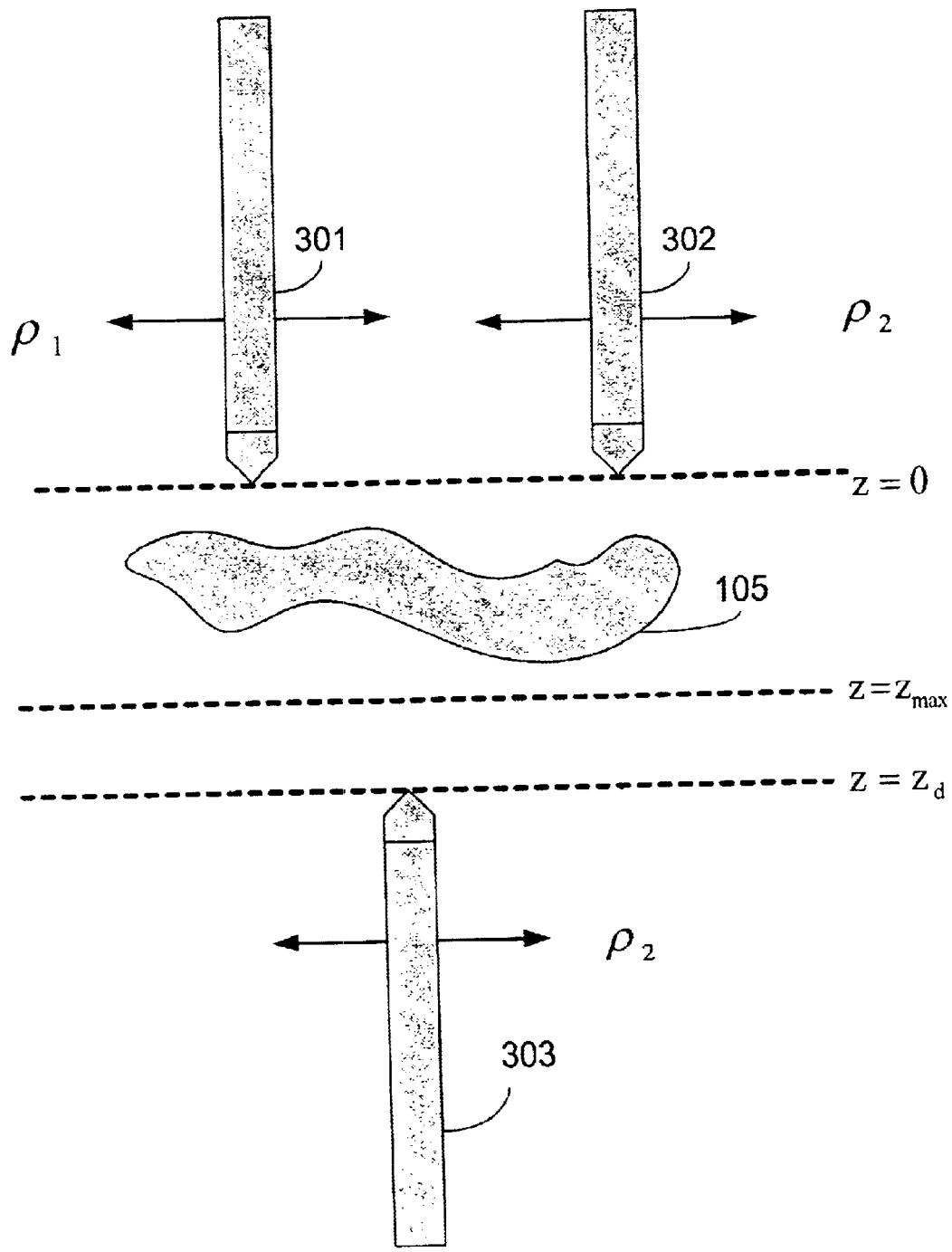
FIG. 3 is a pictorial representation for the two-probe mode showing an object under test.

Now the case wherein both the source of illumination and the detector of the scattered field are in the near-zone of the scatterer is considered. The source of illumination is taken to be a point source in the z=0 plane with position $r_1 = (\rho_1, 0)$. By way of notation, the case that the scattered field is measured on the $z = z_d$ plane with $z_d = 0$ is referred to as reflection mode detection, and the case that the scattered field is measured on some plane $z=z_d$ with $z_d>0$ is the transmission mode case. In either mode, the detector position in the $z=z_d$ plane is denoted $r_2=(\rho_2,z_d)$. This arrangement is shown pictorially in FIG. 3 wherein probe 301 is representative of a source of illumination for sample 105. Probe 302 is the detector for the reflection mode, whereas probe 302 is the detector for the transmission mode.

The incident field is given by equation (10). Consequently, the scattered field is given by $$U_s(r_1,r_2)=k_0^2 \int d^3 r G(r_2-r)\eta(r)G(r-r_1). \qquad (21)$$

Taking the Fourier transform over both spatial coordinates $$\Phi_3(q_1,q_2) = \qquad (22)$$

$$\frac{1}{(2\pi)^2} \int d^2\rho_1 d^2\rho_2 \exp[i(q_1 \cdot \rho_1 - q_2 \cdot \rho_2)] U_s(\rho_1, 0; \rho_2, z_d),$$

and using the plane wave decomposition of equation (9), the following obtains:

$$\Phi_3(q_1,q_2) = -\frac{k_0^2 e^{ik_z(q_2)z_d}}{k_z(q_1)k_z(q_2)} \int d^3 r \exp\{i(q_1-q_2)\cdot\rho + \qquad (23)$$

$$i[k_z(q_1)-\epsilon k_z(q_2)]z\}\eta(r).$$

3. Near-Field Inverse Scattering Problem: Scalar Case

In the near-field inverse scattering problem (ISP), the dielectric susceptibility or scattering function $\eta(r)$ is reconstructed from measurements of the scattered field. It may be observed that equations (16), (20) and (23) are all of similar form. In order to describe the inverse scattering problem for all three modalities to be discussed, the following data function is introduced:

$$\Phi(q_1,q_2)=w(q_1,q_2)\int d^3 r \exp\{i(q_1-q_2)\cdot\rho+i[k_z(q_1)-\epsilon k_z(q_2)]\}\eta(r), \qquad (24)$$

where $$\Phi(q_1,q_2)=\Phi_1(q_1,q_2) \text{ for the illumination mode,} \qquad (25a)$$

$$\Phi(q_1,q_2)=\Phi_2(-q_2,-q_1) \text{ for the collection mode,} \qquad (25b)$$

$$\Phi(q_1,q_2)=\Phi_3(q_1,q_2) \text{ for the two probe mode.} \qquad (25c)$$

Through appropriate choice of the weighting function $w(q_1,q_2)$ all three data functions, $\Phi_1$, $\Phi_2$, and $\Phi_3$ may be simply related to $\Phi$, that is, $$w(q_1,q_2) = \frac{ik_0^2}{k_z(q_1)} \text{ for the illumination mode,} \qquad (26a)$$

$$w(q_1,q_2) = \frac{ik_0^2}{k_z(q_2)} \text{ for the collection mode, and} \qquad (26b)$$

$$w(q_1,q_2) = \frac{k_0^2 e^{ik_z(q_2)z_d}}{k_z(q_1)k_z(q_2)} \text{ for the two probe mode.} \qquad (26c)$$

In all cases, it is assumed that the scattered field can be measured with point-like detection and that the measurement yields both amplitude and phase.

The immediate focus is on the derivation of the singular value decomposition (SVD) of the operator relating $\Phi$ to $\eta$ as defined by integral equation (24). The SVD provides considerable insight into the structure of the forward scattering problem. It also provides a direct technique to construct the pseudo-inverse of the scattering operator. The pseudo-inverse may be used to construct the unique solution to the inverse problem with minimum $L^2$ norm. In addition to the construction of the minimum norm solution, the SVD presents an obvious procedure by which to regularize the pseudo-inverse through filtering small singular values. This is a significant point for the near-field ISP because of the presence of evanescent waves which exhibit exponential decay. This exponential behavior is a reflection of the ill-posed nature of the problem.

To commence, write equation (24) as $$\Phi(q_1,q_2)=\int d^3 r K(q_1,q_2;r)\eta(r), \qquad (27)$$

where the forward scattering operator $K(q_1,q_2;r)$ is given by $$K(q_1,q_2;r)=w(q_1,q_2)\exp\{i(q_1-q_2)\cdot\rho+i[k_z(q_1)-\epsilon k_z(q_2)]z\}. \qquad (28)$$

It is desired to find the SVD of K which is of the form $$K(q_1,q_2;r)=\int d\sigma\sigma F_\sigma^*(r) G_\sigma(q_1,q_2) \qquad (29)$$

where $\sigma$ is the singular value associated with the singular functions $F_\sigma$ and $G_\sigma$. The singular values and singular functions satisfy the relations $$\int d^3 r K(q_1,q_2;r) F_\sigma(r)=\sigma G_\sigma(q_1,q_2), \qquad (30)$$

and $$\int d^2 q_1 \int d^2 q_2 K^*(q_1,q_2;r) G_\sigma(q_1,q_2)=\sigma F_\sigma(r). \qquad (31)$$

Equations (30) and (31) are sufficient to define the singular functions and singular values. It is also possible to derive from these equations the identities $$K^*KF_\sigma=\sigma^2 F_\sigma, \qquad (32)$$

$$KK^*G_\sigma=\sigma^2 G_\sigma. \qquad (33)$$

Here, K is the integral operator whose kernel is $K(q_1,q_2;r)$. The $F_\sigma$ and $G_\sigma$ are thus the eigenfunctions with eigenvalue $\sigma^2$ of $K^*K$ and $KK^*$, respectively.

To obtain the singular values and singular functions, it is worthwhile to first consider the restricted problem wherein $q_2$ is fixed and obtain the SVD of $K(q_1,q_2;r)$ which for fixed $q_2$ is denoted $K_{q_2}(q_1,r)$. Then the following obtains:

$$K_{q_2}(q_1,r)=\int d^2 Q \sigma_Q^{q_2} f_Q^{q_2*}(r) g_Q^{q_2}(q_2), \qquad (34)$$

$$K_{q_2} f_Q^{q_2}=\sigma_Q^{q_2} g_Q^{q_2}, \qquad (35)$$

$$K_{q_2}^\dagger g_Q^{q_2}=\sigma_Q^{q_2} f_Q^{q_2}, \qquad (36)$$

where the $f_Q^{q_2}$ and $g_Q^{q_2}$ are the singular functions for fixed $q_2$ with singular value $\sigma_Q^{q_2}$, labeled by the two dimensional vector Q. The eigenvalue equations then become $$K_{q_2}^\dagger K_{q_2} f_Q^{q_2}=(\sigma_Q^{q_2})^2 f_Q^{q_2}, \qquad (37)$$

$$K_{q_2} K_{q_2}^\dagger g_Q^{q_2}=(\sigma_Q^{q_2})^2 g_Q^{q_2}. \qquad (38)$$

By inspection, it is seen that $$g_Q^{q_2}(q_2)=\delta(Q+q_2-q_1), \qquad (39)$$

$$f_Q^{q_2}(r)=(\sigma_Q^{q_2})^{-1} w^*(q_2+Q,q_2)\exp\{-iQ\cdot\rho-i[k_z^*(q_2+Q)-\epsilon k_z^*(q_2)]z\}. \qquad (40)$$

(Note that an explicit expression for $\sigma_Q^{q_2}$ may be obtained but is not needed.) The $f_Q^{q_2}$ are orthogonal for fixed $q_2$, $$<f_Q^{q_2}|f_{Q'}^{q_2}>=\delta(Q-Q'). \qquad (41)$$

The $f_Q^{q_2}$ are also orthogonal for different $q_2$, that is, $$\langle f_Q^{q_2} | f_{Q'}^{q'_2} \rangle = (\sigma_Q^{q_2} \sigma_{Q'}^{q'_2})^{-1} M(q_2, q'_2; Q) \delta(Q-Q'), \quad (42)$$

which defines $M(q_2, q'_2; Q)$

Returning now to the main problem of finding the SVD of $K(q_1, q_2; r)$, make the ansatz that the G's are constructed from the $g_Q^q$:

$$G_{QQ'}(q_1, q_2) = C_{Q'}(q_2; Q) g_Q^{q_2}(q_1), \quad (43)$$

where the singular values and the singular functions are labeled with two-dimensional vectors, Q and Q'. Making use of the relation $$KK^* G_{QQ'} = \int d^2 q K_q K_q^* \cdot G_{QQ'} \quad (44)$$

it is found that equations (33) and (38) imply that $$\int d^2 q' M(q, q'; Q) C_{Q'}(q'; Q) = \sigma^2_{QQ'} C_{Q'}(q; Q). \quad (45)$$

That is, $C_{Q'}(q; Q)$ is an eigenfunction of $M(Q)$ labeled by $Q'$ with eigenvalue $\sigma^2_{QQ'}$. Since $M(Q)$ is Hermitian, the $C_{Q'}(q; Q)$ may be taken to be orthonormal. It then follows from equation (31) that $$F_{QQ'}(r) = \sigma_{QQ'}^{-1} \int d^2 q C_{Q'}(q; Q) \sigma_Q^q f_Q^q(r). \quad (46)$$

Thus the SVD of $K(q_1, q_2; r)$ is given by $$K(q_1, q_2; r) = \int d^2 Q d^2 Q' \sigma_{QQ'} F_{QQ'}^*(r) G_{QQ'}(q_1, q_2). \quad (47)$$

An explicit evaluation of $M(Q)$ shows that $M(q, q'; Q)$ is divergent when $|q|, |q'|, |Q+q|$, and $|Q+q'|$ are all less than $k_0$ and also in the case of transmission mode when $k_z(Q+q) + k_z(Q+q') \geq k_z(q) + k_z(q')$. Of course, this divergence is unphysical. Any scatterer must be of finite thickness and so, to avoid divergencies, the integration over r is limited to the region $0 \leq z \leq z_{max}$. Then $M(Q)$ takes the explicit form $$M(q, q'; Q) = i 4\pi^2 w*(q, Q+q) w(q', Q+q') \times \quad (48)$$

$$\frac{1 - \exp\{i(\epsilon k_z^*(Q+q) + k_z^*(q) - \epsilon k_z(Q+q') - k_z(q')) z_{max}\}}{\epsilon k_z^*(Q+q) + k_z^*(q) - \epsilon k_z(Q+q') - k_z(q')}.$$

In practice, specification of $z_{max}$ acts as a means for including some prior knowledge about the sample 105 in the model.

3A. The Pseudo-inverse

To reconstruct $\eta(r)$ from the data function $\Phi(q_1, q_2)$ it is necessary to first solve the integral equation $K\eta = \Phi$. Since $\eta$ and $\Phi$ belong to different Hilbert spaces, the inverse of K as a linear operator is not defined. Instead, a substitute for the solution is sought which is defined to be a minimizer of $\|K\eta - \Phi\|$. Among all such solutions, it is conventional to choose the one with minimum $L^2$ norm. This so-called pseudo inverse solution $\eta^+(r)$ is unique and is given by $$\eta^+(r) = \int d^2 q_1 d^2 q_2 K^+(r; q_1, q_2) \Phi(q_1, q_2), \quad (49)$$

where $K^+(r; q_1, q_2)$ is the pseudo-inverse of $K(q_1, q_2; r)$. The pseudo-inverse may be obtained from the SVD of K and is given by the following $$K^+(r; q_1, q_2) = \int d^2 Q d^2 Q' \frac{1}{\sigma_{QQ'}} F_{QQ'}(r) G_{QQ'}^*(q_1, q_2). \quad (50)$$

Using the explicit expressions obtained for the singular functions, $K^+$ is found to be given by $$K^+(r; q_1, q_2) = \int d^2 Q \int d^2 Q' \int d^2 q \delta(Q + q_2 - q_1) \times \sigma_{QQ'}^{-2} C_{Q'}(q; Q) C_{Q'}^*(q_2; Q) w^*(q+Q, q) \times \exp\{-iQ \cdot \rho - i(k_z^*(q+Q) - \epsilon k_z^*(q))z\}. \quad (51)$$

It may be noted that $$\int d^2 Q' \frac{1}{\sigma_{QQ'}^2} C_{Q'}(q; Q) C_{Q'}^*(q_2; Q) = M^{-1}(q, q'; Q), \quad (52)$$

where $M^{-1}(q, q'; Q)$ is the qq' matrix element of $M^{-1}(Q)$. Thus $$\eta^+(r) = \int d^2 q_1 d^2 q_2 \int d^2 Q d^2 q \delta(Q+q_2-q_1) M^{-1}(q, q'; Q) w^*(q+Q, q) \times \exp\{-iQ \cdot \rho - i(k_z^*(q+Q) - \epsilon k_z^*(q))z\} \Phi(q_1, q_2), \quad (53)$$

which is the inversion formula for the near-field ISP.

3B. Regularization

It is known in the art that the singular values for K may be very small and the ISP is ill-posed. Accordingly, the kernel $K^+$ is highly singular and must be regularized to obtain a stable image reconstruction algorithm. Any of the standard approaches, such as Wiener filtering or the Tikhonov techniques, may be used. For the SVD-derived pseudo-inverse, these methods result in modification of the singular values via the introduction of a suitable regularizer $R(\sigma)$. More explicitly, equation (50) is can be written as $$K^+(r; q_1, q_2) = \int d^2 Q d^2 Q' \frac{1}{\sigma_{QQ'}} R(\sigma_{QQ'}) F_{QQ'}(r) G_{QQ'}^*(q_1, q_2). \quad (54)$$

The simplest choice of $R(\sigma)$ consists of simple truncation, which leads to $$R(\sigma_{QQ'}) = \sigma_{QQ'}^{-1} \theta(\sigma_{QQ'}^{-1} - \sigma_{min}), \quad (55)$$

for some $\sigma_{min}$. As a variant of this approach, the regularizer may be $$R(\sigma_{QQ'}) = \sigma_{QQ'}^{-1} \theta(\sigma_{QQ'}^{-1} - \beta \max_Q(\sigma_{QQ'})), \quad (56)$$

where $\beta$ is the regularization parameter and $\max_Q(\sigma_{QQ'})$ is the largest singular value for a fixed Q. This has the effect of conditioning each of the matrices $M(Q)$ individually. If Tikhonov regularization is used, $$R(\sigma_{QQ'}) = \frac{\sigma_{QQ'}}{\lambda + \sigma_{QQ'}^2}, \quad (57)$$

where $\lambda$ is a regularization parameter. This choice leads to smoothing of $\eta^+(r)$ by penalizing functions with large $L^2$ norm.

4. Vector Scattering Theory

Now the attention is focused on the vector theory of light. The mathematical treatment of the vector near-field ISP is quite similar to the scalar case; reference is made to the scalar case as needed. Nevertheless, the full vector theory is necessary to consider in depth because the scalar approximation of the scattering of electromagnetic waves breaks down for the case of the dielectric susceptibility $\eta(r)$ varying on subwavelength scales. In addition, the vector approach allows for the incorporation of effects due to polarization.

The attention is on non-magnetic materials, so the focus is only on the electric field E. Consider a monochromatic field of frequency $\omega$. The electric field then satisfies the reduced wave equation $$\nabla \times \nabla \times E(r) - k_0^2 E(r) = 4\pi k_0^2 \eta(r) E(r), \tag{58}$$

where $\eta(r)$ is the dielectric susceptibility. The field is taken to be composed of two parts, $$E(r) = E^i(r) + E^s(r), \tag{59}$$

where $E^i(r)$ is the incident field satisfying the homogeneous equation $$\nabla \times \nabla \times E^i(r) - k_0^2 E^i(r) = 0, \tag{60}$$

and $E^s(r)$ is the scattered field satisfying the equation $$\nabla \times \nabla \times E^s(r) - k_0^2 E^s(r) = 4\pi k_0^2 \eta(r) E(r). \tag{31}$$

Equation (61) may be recast in integral form $$E_\alpha^s(r) = k_0^2 \int d^3r' G_{\alpha\beta}(r-r') E_\beta(r') \eta(r'), \tag{62}$$

where $G_{\alpha\beta}$ is the electromagnetic free-space Green's tensor satisfying the equation $$\nabla \times \nabla \times G_{\alpha\beta}(r) - k_0^2 G_{\alpha\beta}(r) = 4\pi \delta(r) \delta_{\alpha\beta}. \tag{63}$$

The following notation is used throughout, namely, Greek subscripts indicate vector components and the summation convention applies to repeated indices.

Within the accuracy of the first Born approximation, the scattered field is given by $$E_\alpha^s(r) = k_0^2 \int d^3r' G_{\alpha\beta}(r-r') E_\beta^i(r') \eta(r'). \tag{64}$$

The Green's tensor may be obtained from the scalar Green's function by observing that $$G_{\alpha\beta}(r) = (\delta_{\alpha\beta} + k_0^{-2} \partial_\alpha \partial_\beta) G(r). \tag{65}$$

Thus it becomes possible to obtain the plane wave decomposition of $G_{\alpha\beta}$ directly by the expression $$G_{\alpha\beta}(r) = \frac{i}{2\pi} \int d^2 Q k_z(Q)^{-1} T_{\alpha\beta}(Q) \exp\{iQ\cdot\rho + ik_z(Q)|z|\}, \tag{66}$$

where $T_{\alpha\beta}(Q)$ accounts for the polarization of the modes and is given by the expression $$T_{\alpha\beta}(Q) = \delta_{\alpha\beta} - k_0^{-2} k_\alpha(Q) k_\beta(Q), \tag{67}$$

and $k(Q) = (Q, \epsilon k_z(Q))$.

4A. Illumination Mode

Now turn to the modality considered in Section 2.A in which sample 105 is illuminated by a point source with position $r_1 = (\rho_1, 0)$ which is scanned in the plane $z=0$. The incident filed is given by $$E_\alpha^i(r) = k_0^2 G_{\alpha\beta}(r-r_1) p_\beta \tag{68}$$

where p is the dipole moment of the source of the incident field. Using equation (64), the scattered field is seen to be of the form $$E_\alpha^s(r) = k_0^4 \int d^3r' G_{\alpha\beta}(r-r') \eta(r') G_{\beta\gamma}(r'-r_1) p_\gamma \tag{69}$$

In the far zone of the scatterer, for $|r| \gg |r'|$, the asymptotic form of the Green's function is given by $$G_{\alpha\beta}(r-r') \sim T_{\alpha\beta}(q) \frac{e^{ikr}}{r} e^{-ik(q)r'}, \tag{70}$$

where equation (12) has been deployed and $k(q)=(q,\epsilon k_z(q))$ is in the direction of r. It is then seen that the scattered field may be expressed in terms of the scattering amplitude $A_{\alpha\beta}(\rho_1, q)$ as $$E_\alpha^s(r) \sim k_0^2 A_{\alpha\beta}(\rho_1, q) p_\beta \frac{e^{ikr}}{r}. \tag{71}$$

Making use of equations (66), (69), and (70), it is found that $$A_{\alpha\beta}(\rho_1,q) = k_0^2 T_{\alpha\gamma}(q) \int d^3r' G_{\gamma\beta}(r'-r_1) \exp[-iq\cdot\rho' - i\epsilon k_z(q)z'] \eta(r'). \tag{72}$$

As before, a data function is defined through a Fourier transform of the angular part of the far-zone scattered field, $$\Phi_\alpha^{(1)}(q_1, q_2) = \frac{1}{2\pi} \int d^2\rho_1 e^{iq_1\cdot\rho_1} A_{\alpha\beta}(\rho_1, q_2) p_\beta. \tag{73}$$

Making use of the plane-wave decomposition equation (66), it is found that $$\Phi_\alpha^{(1)}(q_1, q_2) = \frac{ik_0^2}{k_z(q_1)} T_{\alpha\gamma}(q_2) T_{\gamma\beta}(q_1) p_\beta \tag{74}$$

$$\int d^3r \exp\{i(q_1 - q_2)\cdot\rho + i[k_z(q_1) - \epsilon k_z(q_2)]z\} \eta(r).$$

It may be noted that $\Phi_\alpha^{(1)}$ is identical to $\Phi_1$ except for the polarization factors, $$\Phi_\alpha^{(1)}(q_1,q_2) = T_{\alpha\gamma}(q_2) T_{\gamma\beta}(q_1) p_\beta \Phi_1(q_1,q_2). \tag{75}$$

4B. Collection Mode

Now consider the modality discussed in Section 2B in which an incident plan wave illuminates sample 105 and the scattered field is measured in the $z=0$ plane. The incident field may be expressed as $$E_\alpha^i(r) = e_\alpha \exp[iq\cdot\rho - i\epsilon k_z(q)z]. \tag{76}$$

where $e_\alpha$ is the polarization incident field. The scattered field, measured in the $z=0$ plane at the position $r=(\rho_d, 0)$, is given by the expression $$E_\alpha^s(\rho,0;q) = k_0^2 \epsilon_\beta \int d^3r' G_{\alpha\beta}(r-r') \exp[iq\cdot\rho' - i\epsilon k_z(q)z'] \eta(r'). \tag{77}$$

Now define the data function as the Fourier transform of the scattered field $$\Phi_\alpha^{(2)}(q_1, q_2) = \frac{1}{2\pi} \int d^2\rho e^{-iq_2\cdot\rho} E_\alpha^s(\rho, 0; q_1), \tag{78}$$

and use the plane wave decomposition equation (66) to obtain the explicit form $$\Phi_\alpha^{(2)}(q_1, q_2) = \tag{79}$$

$$\frac{ik_0^2}{k_z(q_2)} T_{\alpha\beta}(q_2) e_\beta \int d^3r \exp\{i(q_1 - q_2)\cdot\rho + i[k_z(q_2) - \epsilon k_z(q_1)]z\} \eta(r).$$

Again it may be seen that $\Phi_\alpha^{(2)}$ and $\Phi_2$ are simply related by the expression $$\Phi_\alpha^{(2)}(q_1,q_2)=T_{\alpha\beta}(q_2)e_\beta\Phi_2(q_1,q_2). \qquad (80)$$

4C. Two Probe Mode

Now the case wherein both the source of illumination and the detector of the scattered field are in the near-zone of the scatterer is considered. The source of illumination is taken to be a point source in the $z=0$ plane with position $r_1=(\rho_1,0)$. By way of notation, the case that the scattered field measured on the $z=0$ plane is referred to as the reflection mode, and the case that the scattered field measured on the plane $z=z_d$ with $z_d>0$ is referred to as the transmission mode case. In either mode, the detector position in the $z=z_d$ plane is denoted $r_2=(\rho_2,z_d)$. The incident field is given by equation (68). Consequently, the scattered field is given by $$E_\alpha^s(\rho_1,0;\rho_2,z_d)=k_0^4\int d^3r'G_{\alpha\beta}(r_d-r')G_{\beta\gamma}(r'-r_1)\rho_\gamma\eta(r'). \qquad (81)$$

Taking the Fourier transform over both spatial coordinates defines a data function $$\Phi_\alpha^{(3)}(q_1, q_2) = \qquad (82)$$

$$\frac{1}{(2\pi)^2}\int d^2\rho_1 d^2\rho_2 \exp[i(q_1\cdot\rho_1 - q_2\cdot\rho_2)]E_\alpha^s(\rho_1,0;\rho_2,z_d).$$

It is then found that the following obtains:

$$\Phi_\alpha^{(3)}(q_1,q_2) = -\frac{k_0^4 e^{i\varepsilon k_z(q_2)z_d}}{k_z(q_1)k_z(q_2)}T_{\alpha\beta}(q_2)T_{\beta\gamma}(q_1)p_\gamma \times \qquad (83)$$

$$\int d^3r \, \exp\{i(q_1-q_2)\cdot\rho + i[k_z(q_1)-\varepsilon k_z(q_2)]z\}\eta(r).$$

The data functions $\Phi_\alpha^{(3)}$ and $\Phi_3$ are simply related by $$\Phi_\alpha^{(3)}(q_1,q_2)=T_{\alpha\beta}(q_2)T_{\beta\gamma}(q_1)p_\gamma\Phi_3(q_1,q_2). \qquad (84)$$

5. Near-Field Inverse Scattering Problem: Vector Case

As in the scalar case, the inverse problem is treated for all three modalities by considering a data function of the form $$\Phi_\alpha(q_1,q_2)=w_\alpha(q_1,q_2)\int d^3r \, \exp\{i(q_1-q_2)\cdot\rho+i[k_z(q_1)-\varepsilon k_z(q_2)]z\}\eta(r) \qquad (85)$$

where $$\Phi_\alpha(q_1,q_2)=\Phi_\alpha^{(1)}(q_1,q_2), \text{ for illumination mode} \qquad (86a)$$

$$\Phi_\alpha(q_1,q_2)=\Phi_\alpha^{(2)}(-q_2,-q_1), \text{ for collection mode} \qquad (86b)$$

$$\Phi_\alpha(q_1,q_2)=\Phi_\alpha^{(3)}(q_1,q_2), \text{ for two-probe mode.} \qquad (86c)$$

Through appropriate choice of the weighting function $w_\alpha(q_1,q_2)$ all three data functions may be simply related to $\Phi_\alpha$, that is, $$w_\alpha(q_1,q_2)=-\frac{ik_0^2}{k_z(q_1)}T_{\alpha\gamma}(q_2)T_{\gamma\beta}(q_1)p_\beta, \text{ illumination mode} \qquad (87a)$$

$$w_\alpha(q_1,q_2)=-\frac{ik_0^2}{k_z(q_2)}T_{\alpha\beta}(q_2)e_\beta, \text{ collection mode} \qquad (87b)$$

$$w_\alpha(q_1,q_2)=-\frac{k_0^4 e^{i\varepsilon k_z(q_2)z_d}}{k_z(q_1)k_z(q_2)}T_{\alpha\beta}(q_2)T_{\beta\gamma}(q_1)p_\gamma, \text{ two-probe mode.} \qquad (87c)$$

The vector integral equation (85) differs from its scalar counterpart of equation (24) only by a factor associated with polarization. It is clear then that by measuring a fixed component of the scattered field that the scalar inversion formula of equation (49) may be used to reconstruct $\eta(r)$. It is advantageous, however, to utilize measurements of all three components of the scattered field. In this case, the ISP is over-determined and the SVD of the operator relating $\Phi_\alpha$ and $\eta$ is needed.

To obtain the required SVD, begin by writing equation (85) as $$\Phi_\alpha(q_1,q_2)=\int d^3r K_\alpha(q_1,q_2;r)\eta(r), \qquad (88)$$

where the forward scattering operator $K_\alpha(q_1,q_2;r)$ for the vector wave case is given by $$K_\alpha(q_1,q_2;r)=w_\alpha(q_1,q_2)\exp\{i(q_1-q_2)\cdot\rho+i[k_z(q_1)-\varepsilon k_z(q_2)]z\}. \qquad (89)$$

Consider first the restricted problem where $q_2$ and $\alpha$ are fixed, and obtain the SVD of the vector operator with components $K_\alpha(q_1,q_2;r)$ which, for fixed $q_2$ and $\alpha$, is denoted $K_{q_2\alpha}(q_1,r)$. The SVD is then obtained as follows:

$$K_{q_2\alpha}(q_1,r)=\int d^2Q\sigma_{Q_\alpha}^{q_2}f_{Q_\alpha}^{q_2*}(r)g_Q^{q_2}(q_2), \qquad (90)$$

where the $f_{Q_\alpha}^{q_2}$ are the singular functions for fixed $q_2$ and $\alpha$ with singular values $\sigma_{Q_\alpha}^{q_2}$. It is readily seen that $$f_{Q_\alpha}^{q_2}=(\sigma_{Q_\alpha}^{q_2})^{-1}w^*(q_2+Q,q_2)\exp\{-iQ\cdot\rho-i[k_z^*(q_2+Q)-\varepsilon k_z^*(q_2)]z\}. \qquad (91)$$

As before, an explicit expression for $\sigma_{Q_\alpha}^{q_2}$ is not required. The $f_{Q_\alpha}^{q_2}$ obey the orthogonality conditions $$\langle f_{Q_\alpha}^{q_2}|f_{Q'_\alpha}^{q_2}\rangle=\delta(Q-Q'), \qquad (92)$$

and $$\langle f_{Q_\alpha}^{q_2}|f_{Q'_\beta}^{q'_2}\rangle=(\sigma_{Q_\alpha}^{q_2}\sigma_{Q'_\beta}^{q'_2})^{-1}M_{\alpha\beta}(q_2,q'_2;Q)\delta(Q-Q'), \qquad (93)$$

which defines $M_{\alpha\beta}(q_2,q'_2;Q)$.

To find the SVD of the vector operator $K(q_1,q_2;r)$, it is necessary to determine the eigenfunctions of $KK^*$ which satisfy $$\sum_\beta K_\alpha K_\beta^* G_{QQ'}^\beta(q_1,q_2) = \sigma_{QQ'}^2 G_{QQ'}^\alpha(q_1,q_2), \qquad (94)$$

where the eigenfunctions $G_{QQ'}(q_1,q_2)$ and the singular values $\sigma_{QQ'}$ have been labeled with two-dimensional vectors $Q$ and $Q'$. Make the ansatz that the $G$'s are constructed from the $g_Q^q$:

$$G_{QQ'}^\alpha(q_1,q_2)=C_{Q'}^\alpha(q_2;Q)g_Q^{q_2}(q_1). \qquad (95)$$

Making use of equation (90), it is found that the $C_{Q'}^\alpha(q_2;Q)$ are eigenfunctions of $M_{\alpha\beta}(q,q';Q)$, $$\int d^2q'M_{\alpha\beta}(q,q';Q)C_{Q'}^\beta(q';Q)=\sigma_{QQ'}^2 C_{Q'}^\alpha(q;Q), \qquad (96)$$

with eigenvalues $\sigma_{QQ'}^2$. Next, note that it follows from equation (93) that $$M_{\alpha\beta}(q,q';Q)=w_\alpha(q+Q,q)w_\beta(q'+Q,q')A(q,q';Q), \qquad (97)$$

where $$A(q,q';Q) = \qquad (98)$$

$$i4\pi^2 \frac{1-\exp\{i(\varepsilon k_z^*(Q+q)+k_z^*(q)-\varepsilon k_z(Q+q')-k_z(q'))z_{max}\}}{\varepsilon k_z^*(Q+q)+k_z^*(q)-\varepsilon k_z(Q+q')-k_z(q')}.$$

Since the prefactor $w_\alpha(q+Q,q)w_\beta(q'+Q,q')$ of $A(q,q';Q)$ has the form of a projection operator, it is found that $C_{Q'}^\alpha(q;Q)$ maybe expressed as $$C_{Q'}^\alpha(q;Q) = \phi_{Q'}(q,Q)\frac{w_\alpha(q+Q,q)}{\Omega(q,Q)}, \quad (99)$$

where $$\Omega(q,Q) = \left(\sum_\alpha |w_\alpha(q+Q,q)|^2\right)^{\frac{1}{2}}. \quad (100)$$

The $\phi_{Q'}(q;Q)$ are easily seen to be the eigenfunctions of $\tilde{A}(q,q';Q)=\Omega(q',Q)A(q,q';Q)\Omega(q,Q)$ with eigenvalues $\sigma_{QQ'}^2$, that is, $$\int d^2q'\tilde{A}(q,q';Q)\phi_{Q'}(q';Q) = \sigma_{QQ'}^2\phi_{Q'}(q;Q). \quad (101)$$

A second class of eigenfunctions of $M_{\alpha\beta}(q,q';Q)$ may also be seen to exist. However, these eigenfunctions have vanishing singular values and do not contribute to the SVD of K.

To complete the development of the SVD, the singular values of $F_{QQ'}(r)$ are required, which as follows from equation (31), are given by $$F_{QQ'}(r) = \sigma_{QQ'}^{-1}\sum_\alpha K_\alpha^* G_{QQ'}^\alpha \quad (102)$$

$$= \sigma_{QQ'}^{-1}\int d^2q\sum_\alpha C_{Q'}^\alpha(q;Q)\sigma_{Q_\alpha}^\beta f_{Q_\alpha}^q(r).$$

Using this result, it is seen that the SVD of $K_\alpha(q_1,q_2;r)$ is given by $$K_\alpha(q_1,q_2;r) = \int d^2Qd^2Q'\sigma_{QQ'}F_{QQ'}{}^*(r)G_{QQ'}{}^\alpha(q_1,q_2). \quad (103)$$

The pseudo-inverse of $K_\alpha(q_1,q_2;r)$ may be obtained from the SVD of $K_\alpha$ and is given be the expression $$K_\alpha^+(r;q_1,q_2) = \int d^2Qd^2Q'\frac{1}{\sigma_{QQ'}}F_{QQ'}(r)G_{QQ'}^{\alpha*}(q_1,q_2). \quad (104)$$

Using the expressions previously obtained for the singular functions, $K_\alpha^+$ is found to be of the form $K_\alpha^+(r;q_1,q_2) = \int$ $d^2Q\int d^2Q'\int d^2q$ $\delta(Q+q_2-q_1)\times\sigma_{QQ'}^{-}$ $2C_{Q'}^{\alpha*}(q_2;Q)C_{Q'}^\beta$ $(q;Q)w_\beta^*(q+Q,q)\times\exp\{-$ $iQ\cdot\rho-i(k_z^*(q+Q)-\epsilon$ $k_z^*(q))z\}. \quad (105)$ Using the fact that $$\int d^2Q'\sigma_{QQ'}^{-2}C_{Q'}^{\alpha*}(q;Q)C_{Q'}^\beta(q';Q) = \quad (106)$$

$$\tilde{A}^{-1}(q,q';Q)\frac{w_\alpha^*(q+Q,q)w_\beta(q'+Q,q')}{\Omega(q,Q)\Omega(q',Q)},$$

and the expression for the pseudo-inverse solution $$\eta^+(r) = \int d^2q_1d^2q_2K_\alpha^+(r;q_1,q_2)\Phi_\alpha(q_1,q_2), \quad (107)$$

the following obtains:

$$\eta^+(r) = \quad (108)$$

$$\int d^2q_1d^2q_2\int d^2Qd^2q\frac{\Omega(q,Q)}{\Omega(q_2,Q)}\delta(Q+q_2-q_1)\tilde{A}^{-1}(q_2,q';Q)$$

$$w_\alpha^*(q_2+Q,q_2)\times$$

$$\exp\{-iQ\cdot\rho-i(k_z^*(q+Q)-\epsilon k_z^*(q))z\}\Phi(q_1,q_2),$$

which is the inversion formula for the near-field ISP.

To this point it has been assumed that the scattered field may be measured in its entirety. It may be the case that only certain components of the scattered field are measured. Let $\hat{\xi}$ be a unit vector in the direction in which the scattered field is measured. The measured quantity will then not be $E_\alpha^s$ but $\hat{\xi}\cdot E^s$. The appropriate data function to consider for all three modalities in then $\Phi(q_1,q_2)=\hat{\xi}\Phi_\alpha(q_1,q_2)$. This modifies the weight function without otherwise changing the analysis.

6A. System

Figure 4:
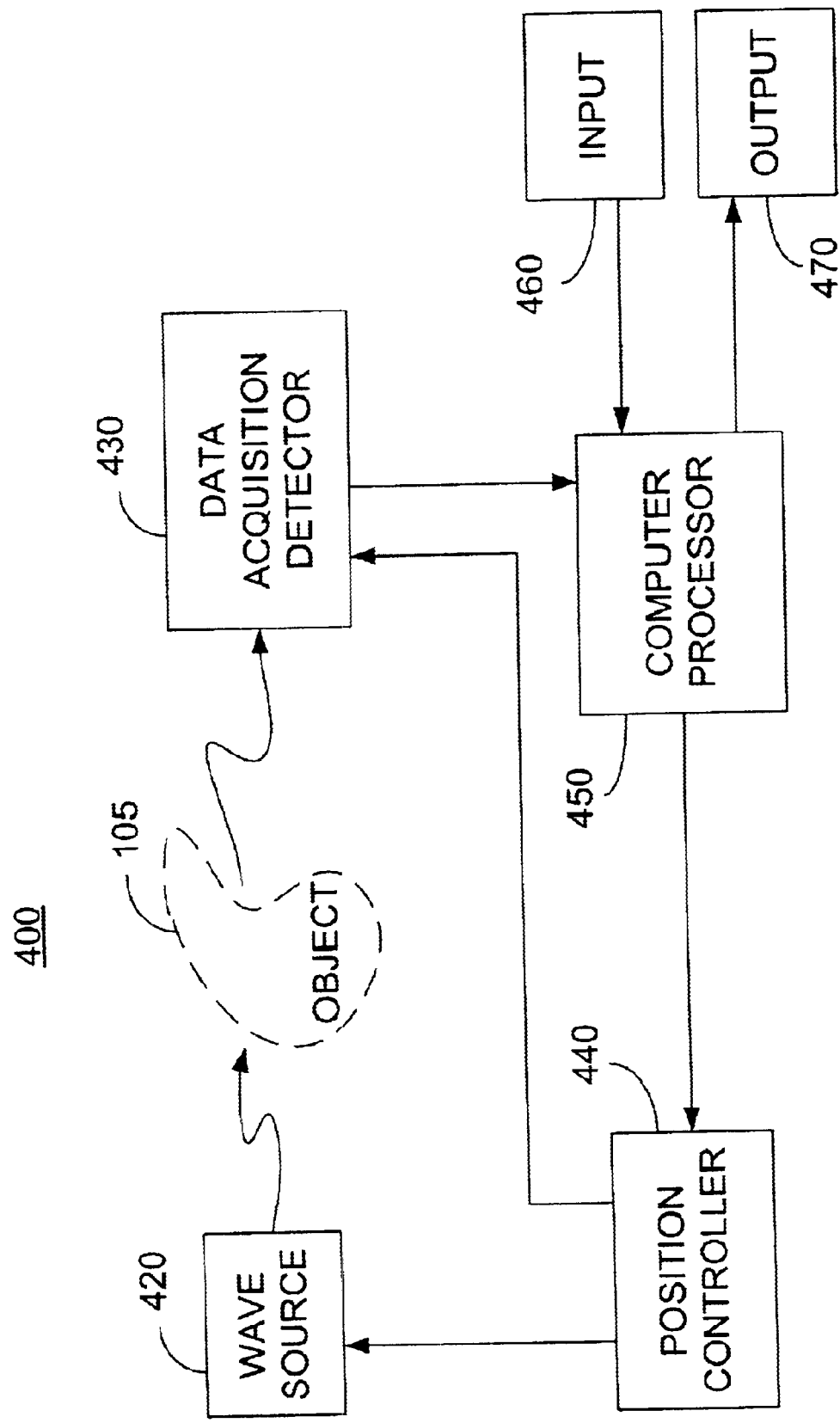
FIG. 4 depicts a system for probing the object with waves to produce scattered waves which are then used to directly reconstruct the image.

As depicted in high-level block diagram form in FIG. 4, system 400 is a tomography system for generating an image of an object using measurements of scattered waves emanating from an object in response to waves illuminating the object. In particular, object 105 is shown as being under investigation. System 400 is composed of: wave source 420 for probing the object 105; data acquisition detector 430 for detecting the scattering data corresponding to the scattered waves from object 105 at one or more locations proximate to object 105; position controller 440 for controlling the locations of detectors 430 and sources 420; and computer processor 450, having associated input device 460 (e.g., a keyboard) and output device 470 (e.g., a graphical display terminal). Computer processor 450 has as its inputs positional information from controller 440 and the measured scattering data from detector 430.

Computer 450 stores a computer program which implements the direct reconstruction algorithm; in particular, the stored program processes the measured scattering data to produce the image of the object or sample under study using a prescribed mathematical algorithm. The algorithm is, generally, determined with reference to an integral operator relating the scattering data to the forward scattering operator (e.g., integral equation (27) wherein the forward scattering operator is $K(q_1,q_2;r)$ or by integral equation (88) wherein the forward scattering operator is $K_\alpha(q_1,q_2;r)$).

6B. Flow Diagram

Figure 5:
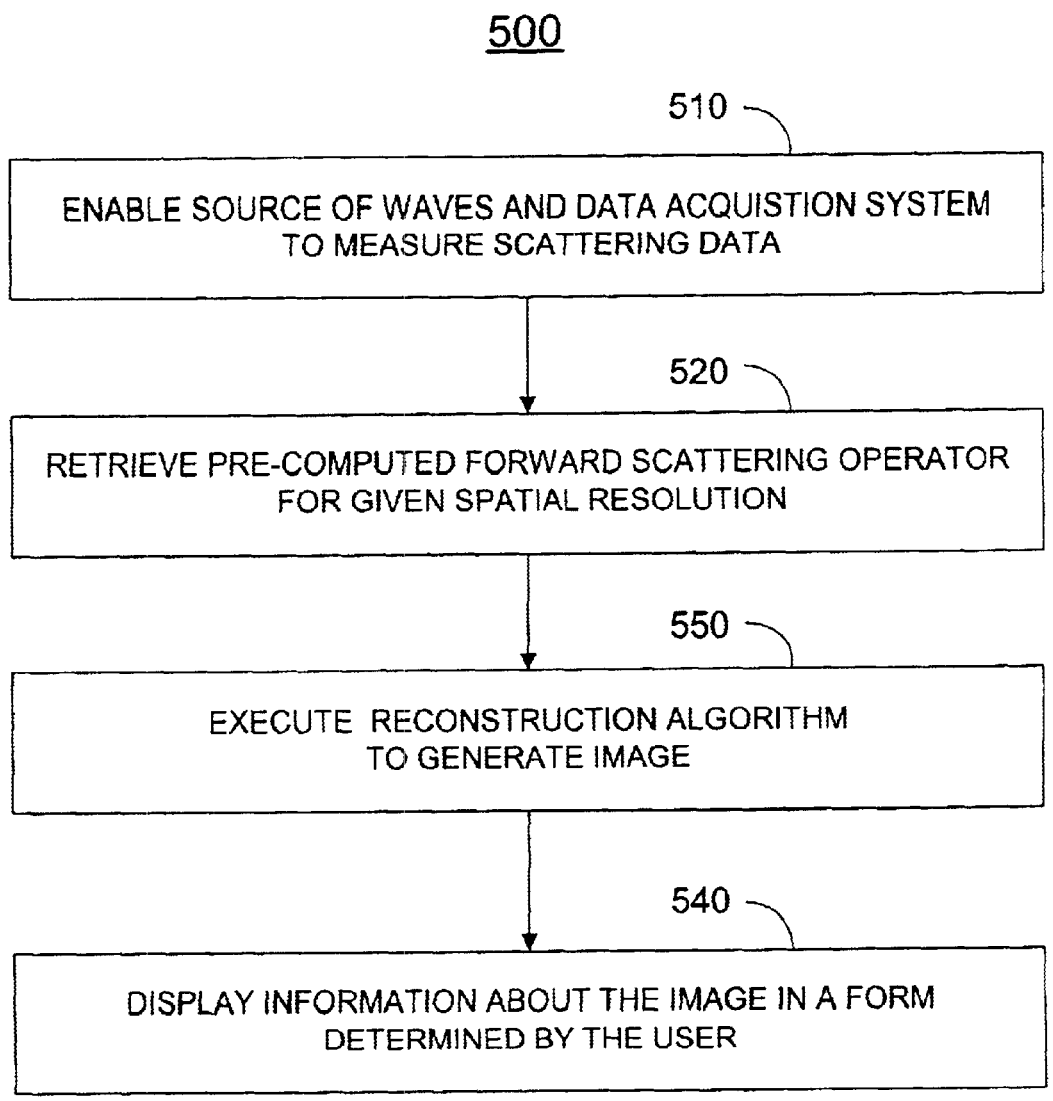
FIG. 5 is a flow diagram for directly reconstructing the image of the object excited by a probing wave.

The methodology carried out by the present invention is set forth in high-level flow diagram 500 of FIG. 5 in terms of the illustrative system embodiment shown in FIG. 4. With reference to FIG. 5, the processing effected by block 510 enables source 420 and data acquisition detector 430 so as to measure the scattering data emanating from object 105 due to illuminating waves from source 420. These measurements are passed to computer processor 450 from data acquisition detector 430 via bus 431. Next, processing block

520 is invoked to retrieve the pre-computed and stored forward scattering operator. In turn, processing block 530 is operated to execute the reconstruction algorithm set forth with respect to the foregoing equations, thereby determining the scattering potential η(r) for the scalar case or dielectric susceptibility η(r) for the electromagnetic case. Finally, as depicted by processing block 540, the reconstructed tomographic image corresponding to η(r) is provided to output device 470 in a form determined by the user; device 470 may be, for example, a display monitor or a more sophisticated three-dimensional display device.

Although the present invention have been shown and described in detail herein, those skilled in the art can readily devise many other varied embodiments that still incorporate these teachings. Thus, the previous description merely illustrates the principles of the invention. It will thus be appreciated that those with ordinary skill in the art will be able to devise various arrangements which, although not explicitly described or shown herein, embody principles of the invention and are included within its spirit and scope. Furthermore, all examples and conditional language recited herein are principally intended expressly to be only for pedagogical purposes to aid the reader in understanding the principles of the invention and the concepts contributed by the inventor to furthering the art, and are to be construed as being without limitation to such specifically recited examples and conditions. Moreover, all statements herein reciting principles, aspects, and embodiments of the invention, as well as specific examples thereof, are intended to encompass both structural and functional equivalents thereof. Additionally, it is intended that such equivalents include both currently know equivalents as well as equivalents developed in the future, that is, any elements developed that perform the function, regardless of structure.

In addition, it will be appreciated by those with ordinary skill in the art that the block diagrams herein represent conceptual views of illustrative circuitry embodying the principles of the invention.

What is claimed is:

1. A method for generating a tomographic image of an object comprising probing the object with incident scalar waves, detecting scattered waves from the object, wherein the scattered waves are detected in a near-field collection mode, and reconstructing the tomographic image by executing a prescribed mathematical algorithm with reference to the incident scalar waves and the scattered waves to generate the tomographic image with sub-wavelength spatial resolution.

2. A method for generating a tomographic image of an object comprising illuminating the object with a source of incident scalar waves, measuring scattering data from the object, wherein the scattering data is measured in a near-field collection mode and is related to the object by an integral operator, and reconstructing the tomographic image by executing a prescribed mathematical algorithm, determined with reference to the integral operator, on the scattering data to produce the tomographic image with sub-wavelength spatial resolution.

3. The method as recited in claim 2 wherein the scattering data is related to the scattering potential of the object by the integral operator, and wherein the reconstructing includes reconstructing the tomographic image by executing the prescribed mathematical algorithm, determined with reference to the integral operator, on the scattering data, the prescribed mathematical algorithm further relating the scattering potential to the scattering data by another integral operator.

4. A method for generating a tomographic image of an object comprising probing the object with incident scalar waves, wherein the incident scalar waves are generated in a near-field illumination mode, detecting scattered waves from the object, wherein the scattered waves are detected in the far-field of the object, and reconstructing the tomographic image by executing a prescribed mathematical algorithm with reference to the incident scalar waves and the scattered waves to generate the tomographic image with sub-wavelength spatial resolution.

5. A method for generating a tomographic image of an object comprising illuminating the object with a source of incident scalar waves, wherein the incident scalar waves are generated in a near-field illumination mode, measuring scattering data from the object, wherein the scattering data is measured in the far-field of the object and is related to the object by an integral operator, and reconstructing the tomographic image by executing a prescribed mathematical algorithm, determined with reference to the integral operator, on the scattering data to produce the tomographic image with sub-wavelength spatial resolution.

6. The method as recited in claim 5 wherein the scattering data is related to the scattering potential of the object by the integral operator, and wherein the reconstructing includes reconstructing the tomographic image by executing the prescribed mathematical algorithm, determined with reference to the integral operator, on the scattering data, the prescribed mathematical algorithm further relating the scattering potential to the scattering data by another integral operator.

7. A method for generating a tomographic image of an object comprising probing the object with incident scalar waves, wherein the incident scalar waves are generated in a near-field illumination mode, detecting scattered waves from the object, wherein the scattered waves are detected in a near-field collection mode, and reconstructing the tomographic image by executing a prescribed mathematical algorithm with reference to the incident scalar waves and the scattered waves to generate the image with sub-wavelength spatial resolution.

8. A method for generating a tomographic image of an object comprising illuminating the object with a source of incident scalar waves, wherein the incident scalar waves are generated in a near-field illumination mode, measuring scattering data from the object, wherein the scattering data is measured in a near-field collection mode and is related to the object by an integral operator, and reconstructing the tomographic image by executing a prescribed mathematical algorithm, determined with reference to the integral operator, on the scattering data to produce the tomographic image with sub-wavelength spatial resolution.

9. The method as recited in claim 8 wherein the scattering data is related to the scattering potential of the object by the integral operator, and wherein the reconstructing includes reconstructing the tomographic image by executing the prescribed mathematical algorithm, determined with reference to the integral operator, on the scattering data, the prescribed mathematical algorithm further relating the scattering potential to the scattering data by another integral operator.

10. A system for generating a tomographic image of an object comprising a source for illuminating the object with incident scalar waves, measurement means for measuring scattering data from the object, wherein the scattering data is measured in a near-field collection mode and is related to the object by an integral operator, and reconstruction means, responsive to the measurement means, for reconstructing the tomographic image by executing a prescribed mathematical algorithm, determined with reference to the integral operator, on the scattering data to produce the tomographic image with sub-wavelength spatial resolution.

11. The system as recited in claim 10 wherein the scattering data is related to the scattering potential of the object by the integral operator, and wherein the reconstruction means includes means for reconstructing the tomographic image by executing the prescribed mathematical algorithm, determined with reference to the integral operator, on the scattering data, the prescribed mathematical algorithm further relating the scattering potential to the scattering data by another integral operator.

12. A system for generating a tomographic image of an object comprising a source for illuminating the object with incident scalar waves, wherein the incident scalar waves are generated in a near-field illumination mode, measurement means for measuring scattering data from the object, wherein the scattering data is measured in the far-field of the object and is related to the object by an integral operator, and reconstruction means, responsive to the measurement means, for reconstructing the tomographic image by executing a prescribed mathematical algorithm, determined with reference to the integral operator, on the scattering data to produce the tomographic image with sub-wavelength spatial resolution.

13. The system as recited in claim 12 wherein the scattering data is related to the scattering potential of the object by the integral operator, and wherein the reconstruction means includes means for reconstructing the tomographic image by executing the prescribed mathematical algorithm, determined with reference to the integral operator, on the scattering data, the prescribed mathematical algorithm further relating the scattering potential to the scattering data by another integral operator.

14. A system for generating a tomographic image of an object comprising a source for illuminating the object with incident scalar waves, wherein the incident scalar waves are generated in a near-field illumination mode, measurement means for measuring scattering data from the object, wherein the scattering data is measured in a near-field collection mode and is related to the object by an integral operator, and reconstruction means, responsive to the measurement means, for reconstructing the tomographic image by executing a prescribed mathematical algorithm, determined with reference to the integral operator, on the scattering data to produce the tomographic image with sub-wavelength spatial resolution.

15. The system as recited in claim 14 wherein the scattering data is related to the scattering potential of the object by the integral operator, and wherein the reconstruction means includes means for reconstructing the tomographic image by executing the prescribed mathematical algorithm, determined with reference to the integral operator, on the scattering data, the prescribed mathematical algorithm further relating the scattering potential to the scattering data by another integral operator.

16. A method for generating a tomographic image of an object comprising probing the object with incident electromagnetic waves, detecting scattered waves from the object, wherein the scattered waves are detected in a near-field collection mode, and reconstructing the tomographic image by executing a prescribed mathematical algorithm with reference to the incident electromagnetic waves and the scattered waves to generate the tomographic image with sub-wavelength spatial resolution.

17. A method for generating a tomographic image of an object comprising illuminating the object with a source of incident electromagnetic waves, measuring scattering data from the object, wherein the scattering data is measured in a near-field collection mode and is related to the object by an integral operator, and reconstructing the tomographic image by executing a prescribed mathematical algorithm, determined with reference to the integral operator, on the scattering data to produce the tomographic image with sub-wavelength spatial resolution.

18. The method as recited in claim 17 wherein the scattering data is related to the dielectric susceptibility of the object by the integral operator, and wherein the reconstructing includes reconstructing the tomographic image by executing the prescribed mathematical algorithm, determined with reference to the integral operator, on the scattering data, the prescribed mathematical algorithm further relating the dielectric susceptibility to the scattering data by another integral operator.

19. A method for generating a tomographic image of an object comprising probing the object with incident electromagnetic waves, wherein the incident electromagnetic waves are generated in a near-field illumination mode, detecting scattered waves from the object, wherein the scattered waves are detected in the far-field of the object, and reconstructing the tomographic image by executing a prescribed mathematical algorithm with reference to the incident electromagnetic waves and the scattered waves to generate the tomographic image with sub-wavelength spatial resolution.

20. A method for generating a tomographic image of an object comprising illuminating the object with a source of incident electromagnetic waves, wherein the incident electromagnetic waves are generated in a near-field illumination mode, measuring scattering data from the object, wherein the scattering data is measured in the far-field of the object and is related to the object by an integral operator, and reconstructing the tomographic image by executing a prescribed mathematical algorithm, determined with reference to the integral operator, on the scattering data to produce the tomographic image with sub-wavelength spatial resolution.

21. The method as recited in claim 20 wherein the scattering data is related to the dielectric susceptibility of the object by the integral operator, and wherein the reconstructing includes reconstructing the tomographic image by executing the prescribed mathematical algorithm, determined with reference to the integral operator, on the scattering data, the prescribed mathematical algorithm further relating the dielectric susceptibility to the scattering data by another integral operator.

22. A method for generating a tomographic image of an object comprising probing the object with incident electromagnetic waves, wherein the incident electromagnetic waves are generated in a near-field illumination mode, detecting scattered waves from the object, wherein the scattered waves are detected in a near-field collection mode, and reconstructing the tomographic image by executing a prescribed mathematical algorithm with reference to the incident electromagnetic waves and the scattered waves to generate the image with sub-wavelength spatial resolution.

23. A method for generating a tomographic image of an object comprising illuminating the object with a source of incident electromagnetic waves, wherein the incident electromagnetic waves are generated in a near-field illumination mode, measuring scattering data from the object, wherein the scattering data is measured in a near-field collection mode and is related to the object by an integral operator, and reconstructing the tomographic image by executing a prescribed mathematical algorithm, determined with reference to the integral operator, on the scattering data to produce the tomographic image with sub-wavelength spatial resolution.

24. The method as recited in claim 23 wherein the scattering data is related to the dielectric susceptibility of the object by the integral operator, and wherein the reconstructing includes reconstructing the tomographic image by executing the prescribed mathematical algorithm, determined with reference to the integral operator, on the scattering data, the prescribed mathematical algorithm further relating the dielectric susceptibility to the scattering data by another integral operator.

25. A system for generating a tomographic image of an object comprising a source for illuminating the object with incident electromagnetic waves, measurement means for measuring scattering data from the object, wherein the scattering data is measured in a near-field collection mode and is related to the object by an integral operator, and reconstruction means, responsive to the measurement means, for reconstructing the tomographic image by executing a prescribed mathematical algorithm, determined with reference to the integral operator, on the scattering data to produce the tomographic image with sub-wavelength spatial resolution.

26. The system as recited in claim 25 wherein the scattering data is related to the dielectric susceptibility of the object by the integral operator, and wherein the reconstruction means includes means for reconstructing the tomographic image by executing the prescribed mathematical algorithm, determined with reference to the integral operator, on the scattering data, the prescribed mathematical algorithm further relating the dielectric susceptibility to the scattering data by another integral operator.

27. A system for generating a tomographic image of an object comprising a source for illuminating the object with incident electromagnetic waves, wherein the incident electromagnetic waves are generated in a near-field illumination mode, measurement means for measuring scattering data from the object, wherein the scattering data is measured in the far-field of the object and is related to the object by an integral operator, and reconstruction means, responsive to the measurement means, for reconstructing the tomographic image by executing a prescribed mathematical algorithm, determined with reference to the integral operator, on the scattering data to produce the tomographic image with sub-wavelength spatial resolution.

28. The system as recited in claim 27 wherein the scattering data is related to the dielectric susceptibility of the object by the integral operator, and wherein the reconstruction means includes means for reconstructing the tomographic image by executing the prescribed mathematical algorithm, determined with reference to the integral operator, on the scattering data, the prescribed mathematical algorithm further relating the dielectric susceptibility to the scattering data by another integral operator.

29. A system for generating a tomographic image of an object comprising a source for illuminating the object with incident electromagnetic waves, wherein the incident electromagnetic waves are generated in a near-field illumination mode, measurement means for measuring scattering data from the object, wherein the scattering data is measured in a near-field collection mode and is related to the object by an integral operator, and reconstruction means, responsive to the measurement means, for reconstructing the tomographic image by executing a prescribed mathematical algorithm, determined with reference to the integral operator, on the scattering data to produce the tomographic image with sub-wavelength spatial resolution.

30. The system as recited in claim 29 wherein the scattering data is related to the dielectric susceptibility of the object by the integral operator, and wherein the reconstruction means includes means for reconstructing the tomographic image by executing the prescribed mathematical algorithm, determined with reference to the integral operator, on the scattering data, the prescribed mathematical algorithm further relating the dielectric susceptibility to the scattering data by another integral operator.

* * * * *